United States Patent
Schumacher et al.

(10) Patent No.: US 6,325,803 B1
(45) Date of Patent: Dec. 4, 2001

(54) METHOD AND APPARATUS FOR MANDIBULAR OSTEOSYNTHESIS

(75) Inventors: Brian S. Schumacher; Kevin T. Stone; Jeffrey A. Duncan, all of Jacksonville, FL (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 0 days.

(21) Appl. No.: 09/394,287

(22) Filed: Sep. 10, 1999

Related U.S. Application Data (63) Continuation-in-part of application No. 09/025,140, filed on Feb. 18, 1998, now Pat. No. 6,129,728.

(51) Int. Cl.$^7$ .................................................. A61B 17/56
(52) U.S. Cl. ............................ 606/71; 606/69; 606/73; 606/104
(58) Field of Search ........................ 606/60, 69, 70, 606/71, 73, 61

(56) References Cited

U.S. PATENT DOCUMENTS

| | | | |
|---|---|---|---|
| 1,105,105 | 7/1914 | Sherman . | |
| 2,489,870 | 11/1949 | Dzus . | |
| 2,494,229 | 1/1950 | Collison . | |
| 2,631,584 | 3/1953 | Purificato . | |
| 3,488,779 | 1/1970 | Christensen . | |
| 4,219,015 | 8/1980 | Steinemann . | |
| 4,429,690 | 2/1984 | Angelino-Pievani . | |
| 4,484,570 | 11/1984 | Sutter et al. ......................... | 606/72 |
| 4,708,132 | 11/1987 | Silvestrini . | |
| 4,903,691 | 2/1990 | Heinl .................................. | 606/70 |
| 4,959,065 | 9/1990 | Arnett et al. ........................ | 606/69 |
| 4,973,332 | 11/1990 | Kummer ............................ | 606/65 |
| 5,108,395 | 4/1992 | Laurain ............................. | 606/61 |
| 5,108,399 | 4/1992 | Eitenmuller et al. ............... | 606/77 |
| 5,129,899 | 7/1992 | Small et al. ........................ | 606/61 |
| 5,147,363 | 9/1992 | Härle ................................. | 606/73 |
| 5,151,103 | 9/1992 | Tepic et al. ........................ | 606/69 |
| 5,180,382 | 1/1993 | Frigg et al. ........................ | 606/65 |
| 5,269,784 | 12/1993 | Mast ................................. | 606/69 |
| 5,303,718 | 4/1994 | Krajicek ............................ | 128/897 |
| 5,358,367 | 10/1994 | Yang ................................. | 411/397 |
| 5,372,598 | 12/1994 | Luhr et al. ......................... | 606/69 |
| 5,403,136 | 4/1995 | Mathys .............................. | 411/310 |
| 5,413,577 | 5/1995 | Pollock ............................. | 606/69 |
| 5,474,551 | 12/1995 | Finn et al. ......................... | 606/61 |
| 5,505,731 | 4/1996 | Tornier .............................. | 606/61 |
| 5,520,690 | 5/1996 | Errico et al. ....................... | 606/61 |
| 5,569,247 | 10/1996 | Morrison .......................... | 606/61 |
| 5,591,167 | 1/1997 | Laurain et al. .................... | 606/61 |
| 5,601,553 | 2/1997 | Trebing et al. .................... | 606/61 |
| 5,601,554 | 2/1997 | Howland et al. .................. | 606/61 |
| 5,607,428 | 3/1997 | Lin .................................... | 606/69 |
| 5,653,710 | 8/1997 | Härle ................................. | 606/73 |
| 5,676,667 | 10/1997 | Hausman .......................... | 606/69 |
| 5,722,976 | * 3/1998 | Brown .............................. | 606/69 |
| 6,007,538 | * 12/1999 | Levin ................................ | 606/71 |

FOREIGN PATENT DOCUMENTS

867422 * 7/1949 (DE) .

* cited by examiner

*Primary Examiner*—David O. Reip

(57) ABSTRACT

A system for mandibular reconstruction generally includes an elongated locking plate having a plurality of internally threaded apertures and a plurality of fasteners. Each fastener includes a main body portion having an upper threaded shaft and a lower threaded shaft. The lower threaded shaft is adapted to engage the mandible. Each fastener further includes a removable head portion internally threaded for engaging the upper shaft portion and externally threaded for engaging a selected one of the internally threaded apertures of the locking plate. In the preferred embodiment, the thread leads of the head portion and lower shaft of the main body portion are identical. A method of mandibular osteosynthesis utilizes the system of osteosynthesis and generally comprises the steps of temporarily securing the elongated locking plate to the mandible with at least one fastener by engaging the threads of the lower portion with the mandible and threadably engaging the head with the locking plate, unthreading the head portion from the main body of the fastener to thereby allow displacement of the locking plate from the mandible without removing the fasteners from the mandible, performing a surgical procedure (e.g., removal of a cancerous growth), and re-securing the elongated plate to the fastener with the removable head portion.

13 Claims, 4 Drawing Sheets

METHOD AND APPARATUS FOR MANDIBULAR OSTEOSYNTHESIS

CROSS-REFERENCE TO RELATED APPLICATION

This is a continuation-in-part of U.S. patent application Ser. No. 09/025,140, filed Feb. 18, 1998 now U.S. Pat. No. 6,129,728.

BACKGROUND OF THE INVENTION

1. Field of the Invention

The present invention relates to surgical applications for the repair of bone fractures and deformities. More particularly, the present invention relates to a method apparatus for mandibular osteosythesis.

2. Discussion of the Related Art

In various orthopedic surgical procedures, it is necessary to align and secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed in the desired position during bone regeneration.

It is known in the art to provide metal plates for the repair of bone fractures. These plates are generally secured to bone portions with screws. Among other applications, such plates and fasteners are used to provide rigid stabilization of orthopedic and craniofacial fractures. The plates conventionally employed for cranial and facial osteosynthesis generally comprise small, generally flat, elongated sections of metal. The sections contain round and perhaps elongated screw holes at various points along their lengths for fastening the sections to bone.

Because no surface of the human skeleton is completely flat, existing plates must be extensively twisted, formed and bent during surgery to conform to portions of the skeleton on which they are to be affixed. Significant time is expended during surgery for shaping and re-shaping metal plates adequately to conform to desire bone surfaces. This additional time increases anesthesia requirements and operating room time and also increases the potential for infection.

In one commonly used technique for mandibular reconstruction, a flat plate is drawn against the surface of the mandible with a plurality of fasteners, thereby bending the plate to a desired shape. Subsequently, the fasteners and plate are removed to allow surgical access to the mandible (e.g. for removal of a cancerous growth). Finally, the plate is again fastened to the mandible by engaging the fasteners with existing holes in the mandible.

While known systems utilizing plates and fasteners for cranial and facial osteosynthesis have proven to be acceptable for certain applications, such systems are nevertheless susceptible to improvements that may enhance their performance. In this regard, many known systems require time consuming surgical attachment. Additionally, known systems which necessitate the insertion, removal and subsequent re-insertion of fasteners into the bone negatively affect fastener purchase. Furthermore, many known techniques for cranial facial osteosynthesis disadvantageously position a plate immediately adjacent to the bone which is particularly susceptible to resorption.

SUMMARY OF THE PRESENT INVENTION

In one form, the present invention relates to a method for mandibular osteosynthesis which includes the general step of securing an elongated locking plate to a bone with a plurality of fasteners each including a main body portion having an upper shaft portion and a lower shaft portion. Each fastener further includes a head member removably attached to the upper shaft portion. The method of the present invention further includes the general step of removing the locking plate from the bone by removing the removable head member of each fastener from its main body portion.

In another form, the present invention comprises a system for osteosynthesis of a mandible including an elongated locking plate and at least one fastener. The elongated locking plate has a plurality of internally threaded apertures. Each of the at least one fastener has a main body portion with an externally threaded lower shaft portion and an upper shaft portion. The at least one fastener further has a head member adapted to removably engage the upper shaft portion. The head member is externally threaded for engaging one of the plurality of internally threaded apertures. The externally threaded shaft portion and the externally threaded head member preferably have a common thread lead and an identical thread pitch.

An advantage of the present invention is the provision of a method and apparatus for mandibular osteosynthesis which quickly and easily contours a plate to the mandible without sacrificing fastener purchase with the bone.

A related advantage of the present invention is the provision of a method and apparatus for mandibular osteosynthesis which incorporates a threaded fastener having a removable head.

Another advantage of the present invention is the provision of a method and apparatus for osteosynthesis which incorporates a locking plate with an upwardly curved forward end that more accurately cooperates with the geometry of the human mandible.

Another advantage of the present invention is the provision of a method and apparatus for mandibular osteosynthesis which incorporates an auxiliary reinforcement member adapted to be removably attached to a locking plate.

Another advantage of the present invention is the provision of a method and apparatus for mandible osteosynthesis which incorporates a plate reinforcement member which may be selectively secured to a locking plate for increased strength in areas of significant loss of bone mass.

A related advantage of the present invention is the provision of a method and apparatus for mandible osteosynthesis which incorporates a mesh reinforcement member which may be attached to a reconstruction plate for providing reinforcement where a resection has been made or significant bone mass is otherwise absent.

DETAILED DESCRIPTION OF THE PRESENT INVENTION

The following description of the preferred embodiment of the present invention is merely exemplary in nature and is in no way intended to limit the invention or its application or uses.

Figures 1, 2:
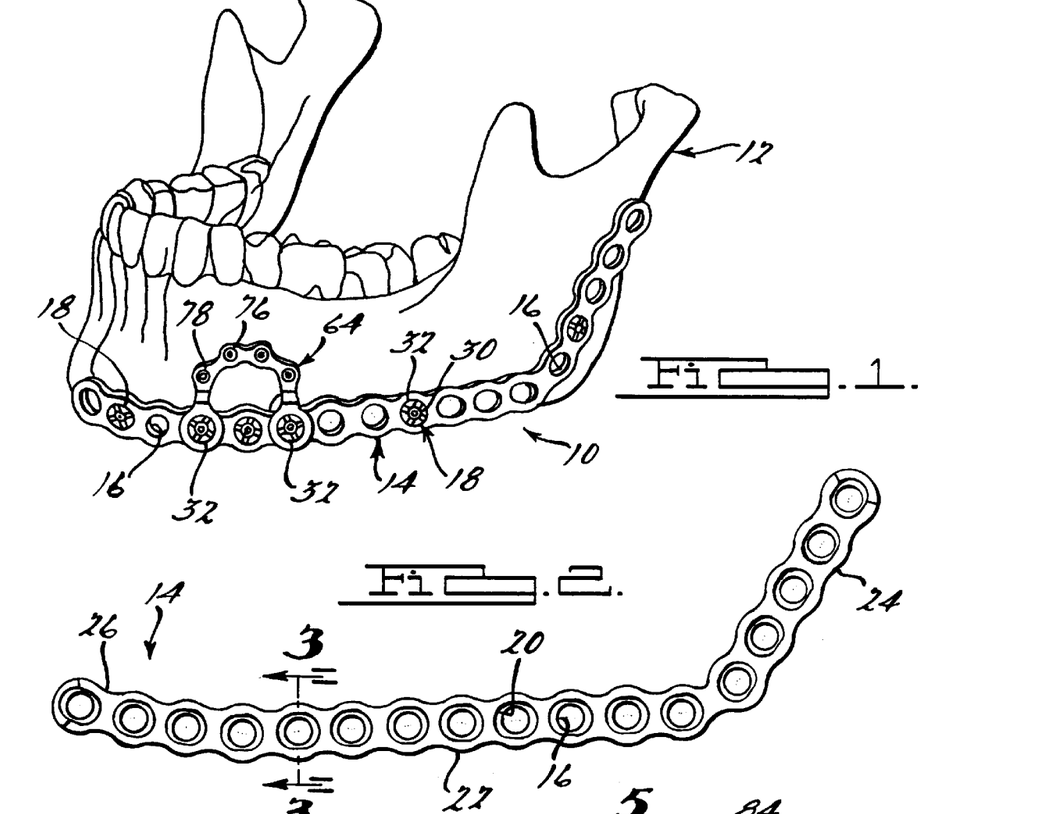
FIG. 1 is a perspective view of a mandibular osteosynthesis system constructed in accordance with the teachings of the preferred embodiment of the present invention illustrated in operative association with a human mandible.
FIG. 2 is an illustration the locking plate shown in FIG. 1 according to the teachings of the preferred embodiment of the present invention.

Referring to FIG. 1, a system constructed in accordance with a preferred embodiment of the present invention is generally identified with reference numeral 10. The system 10 is shown operatively associated with a human mandibular 12. However, it will become apparent to those skilled in the art that certain aspects of the present invention have applicability for other surgical applications.

Figure 3:
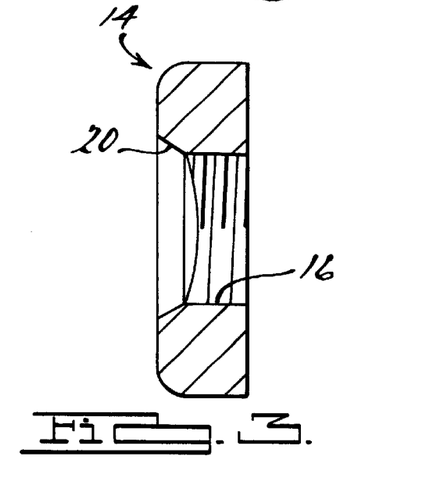
FIG. 3 is a cross-sectional view taken along the line 3—3 of FIG. 2.

With continued reference to FIG. 1 and additional references to FIGS. 2 and 3, the system 10 of the present invention is shown to include an elongated reconstruction plate 14. The plate 14 is formed to include a plurality of apertures 16, each adapted to receive a fastener 18 for interconnecting the plate 14 with the mandible 12. The apertures preferably include an oval countersink 20 and are internally threaded. For this reason, the plate 14 will be interchangeably referred to herein as a locking plate 14.

The locking plate 14 is shown to generally include a central portion 22, and first and second ends 24 and 26. The first end 24 is precontoured in an anterior-posterior direction to cooperate with the shape of the mandible 12. The second end 24 is also curved upwardly in the plane of the central portion 22, this curvature of the second end 26 cooperates with the contour of the human mandible 12 when the locking plate 14 follows the shape of the mandible 12 in a medial-lateral direction.

In one application, the locking plate 14 is constructed of titanium. More preferably, the locking plate 14 is constructed from commercially pure, grade 2 or grade 4 titanium. However, it will be appreciated by those skilled in the art that other materials having suitable performance characteristics may be employed. Preferably, the locking plate 14 is inelastically deformable so as to retain its shape once contoured to cooperate with the shape of the mandible 12.

Figure 4:
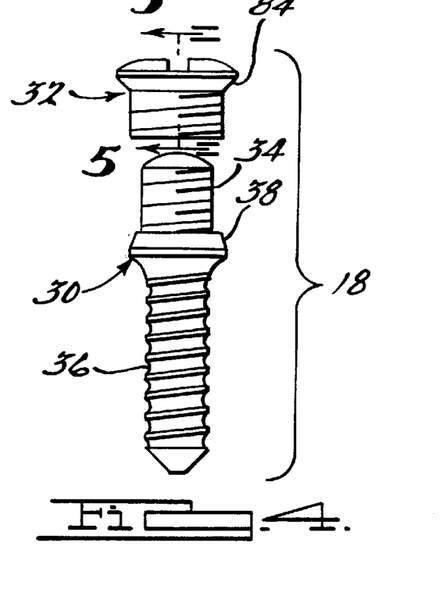
FIG. 4 is an exploded view of one of the fasteners shown in FIG. 1 according to the teachings of the preferred embodiment of the present invention.
Figure 5:
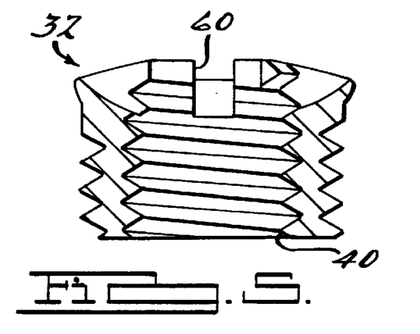
FIG. 5 is a cross-sectional view taken along the line 5—5 of FIG. 4.
Figure 6:
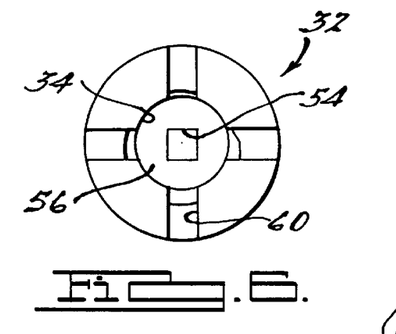
FIG. 6 illustrates an end view of the head of the fastener shown in FIG. 4 according to the teachings of the preferred embodiment of the present invention.

With additional reference to FIGS. 4–6, the fastener 18 of the present invention is shown to generally include a main body 30 and a head member 32. The main body 30 includes an upper shaft portion 34 and a lower shaft portion 36. The lower shaft portion 36 is externally threaded and adapted to engage the mandible or bone 12 in a conventional manner. Insertion of the lower shaft portion into the bone is limited by a flange 38 interdisposed between the upper and lower shaft portions 34 and 36. The upper shaft portion 32 is also externally threaded and adapted to engage an internally threaded aperture 40 of the head member 32. The head member 32 is externally threaded for engaging one of the plurality of internally threaded apertures 16 of the locking plate 14.

In one application, the thread pitches of the upper shaft portion 34, lower shaft portion 36 and the thread pitch of the external threads of the head member 32 are common. The external threads of the head member 32 and the externally threaded lower shaft portion 36 have a common thread lead. In the exemplary embodiment illustrated, the externally threaded lower shaft portion 36 has a single lead configuration while the external threads of the upper shaft portion 34 and head member 32 have a double lead configuration.

In use, a malleable template (not shown) is position on the mandible 12 and bent to the general shape of the cooperating bone surface. Next, the locking plate 14 is bent to approximately the shape of the template and positioned on the mandible 12 so that certain apertures 16 may be selectively used as a guide for drilling holes (not specifically shown) in the mandible 12 for receiving the fasteners 18. A first of the fasteners 18 is passed through a selected one of the apertures 16 and rotated so that the externally threaded lower portion 36 is driven into the hole in the mandible 12. For example, the first end 24 of the locking plate 14 may be first secured to the mandible 12 with a first fastener 18. As the externally threaded lower portion 36 of the fastener 18 is driven into the bone 12, the external threads of the head member 32 simultaneously engage the internally threaded aperture 16 of the locking plate 14. This is possible as a result of the common thread lead shared between the lower portion 36 and the head member 32.

Additional fasteners 18 are used to interconnect the locking plate 14 with the bone 12 in a substantially identical manner. As shown in FIG. 1, four (4) fasteners are used to interconnect the locking plate 14 with the bone 12. However, it will be appreciated by those skilled in the art that any number of fasteners 18 may be employed depending on a particular application. In one application, the order of the fastener insertion linearly progresses along the locking plate 14 from one end (e.g. the first end 24) to the second end (e.g. the second end 26). As additional fasteners are engaged with the bone 12, the locking plate 14 is drawn into its operative position adjacent to the bone 12.

At this point of the surgical procedure, the head members 32 of each of the threaded fasteners 18 are unthreaded from their respective upper portions 34. This allows the surgeon to displace the locking plate 14 from the fasteners 18 and provides access to the bone 12 for accomplishing a desired surgical procedure (e. g., removal of a cancerous growth). When the locking plate 14 is removed, it retains its shape due to go the inelastic deformation. When the surgical procedure is complete, the locking plate 14 is replaced by inserting the upper portions 34 of the fasteners 18 through the selective apertures 14 and simultaneously threading the internal threads of the aperture 16 with the external threads of the upper portion 34 and the external threads of the head member 32 with the internal threads of the aperture 16. Since the fasteners 18 are not removed from the bone 12 after initial insertion, fastener/bone purchase is not compromised.

Figures 11, 12, 13, 14, 15:
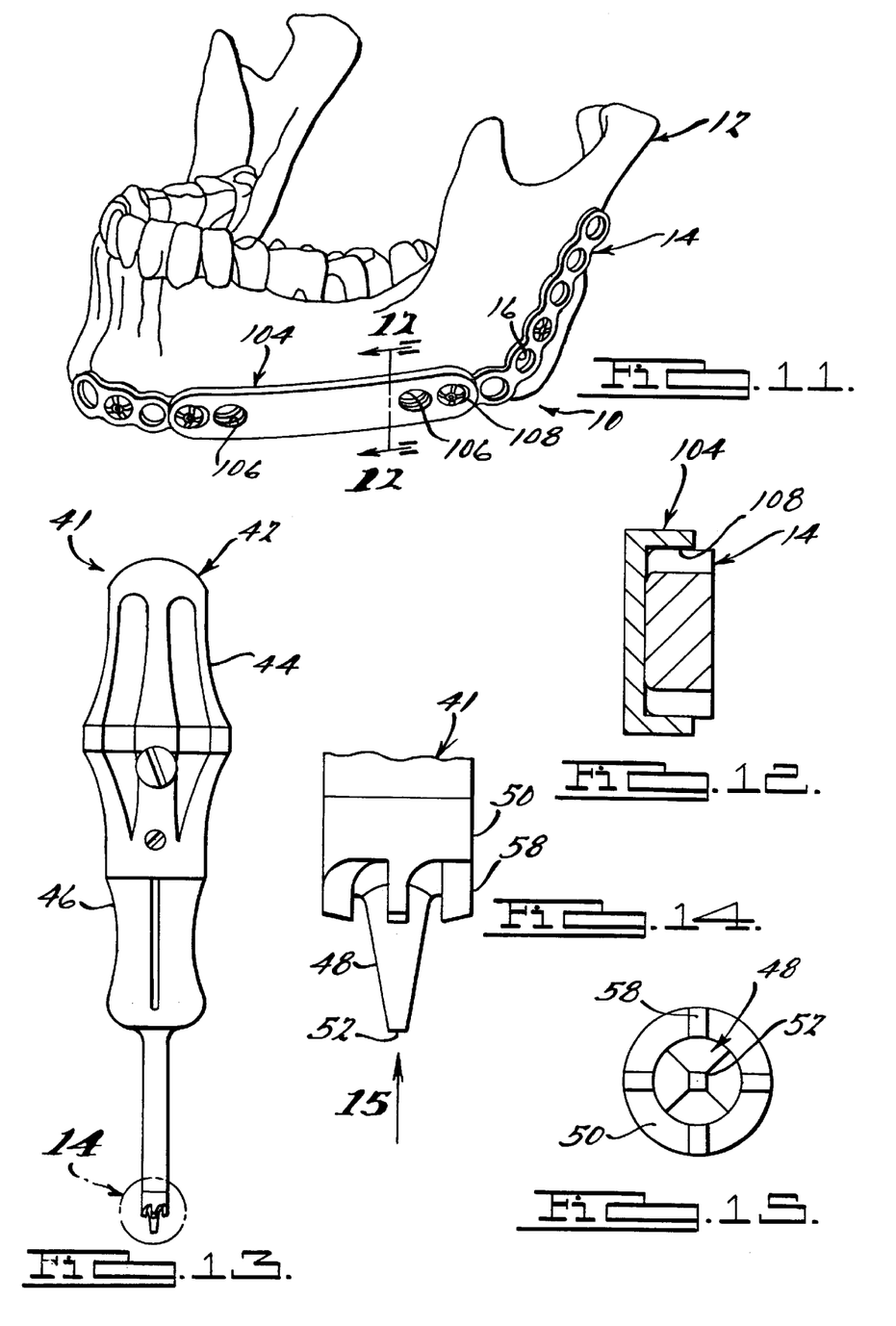
FIG. 11 is a perspective view similar to FIG. 1, illustrating an alternative locking plate and an alternative auxiliary reinforcement member of the mandibular osteosynthesis system of the present invention operatively associated with a human mandible.
FIG. 12 is a cross-sectional view taken along the line 12—12 of FIG. 11.
FIG. 13 is an illustration of a tool of the andibular osteosynthesis system of the present invention.
FIG. 14 is an enlarged view illustrating the detail shown in circle 14 identified in FIG. 13.
FIG. 15 is an enlarged end view of the tool taken in the direction of arrow 15 shown in FIG. 14.

With reference to FIGS. 13–15, one suitable tool for use in connection with the system 10 of the present invention is shown and generally identified with reference numeral 40. The tool includes a handle 42 having an upper portion 44 and a lower portion 46. The upper and lower portions 44 and 46 are rotatable relative to one another about a longitudinal axis of the tool 40. The upper portion 44 is adapted to rotate with a first drive portion 48, while the lower portion 46 of the handle 42 is adapted to rotate with a second drive portion SO. The first drive portion 48 includes a generally rectangular tip 52 adapted to engage a generally rectangular aperture 54 provided in a top surface 56 of the upper shaft portion 34 of each fastener 18. The second drive portion 50 is illustrated to include four (4) drive elements equally spaced about the first drive member 48. The drive elements 58 are adapted to engage a corresponding number of slots 60 equally spaced about the head member 32 of each fastener 18.

After the holes are drilled into the mandible 12, the surgeon selects a fastener with the head portion 32 threaded onto the upper shaft portion 34 of the main body 30 and engages the drive elements 58 of the tool 40 with the slots 60 of the head member 32 simultaneously. Simultaneously, the tip 52 of the drive member 48 engages the rectangular aperture 54 of the upper shaft portion 34. The surgeon grasps the upper and lower portions 44 and 49 of t[]he handle 42 and rotates the tool 40 in a conventional manner. This action causes the head member 32 to threadably engage an aperture 16 of locking plate 14 and simultaneously causes the threads of the lower shaft portion 36 of the fastener 18 to engage the hole provided in the bone 12.

Once all of the fasteners 18 are initially inserted into the bone 12, the surgeon again engages the head 32 with the drive elements 58. The thumb and forefinger are used to rotate the lower portion 46 of the handle 42 and in turn the rotate the head portion 32 of the fastener 18 in a counter-clockwise direction. Simultaneously, the palm and remaining fingers grasp the upper portion 44 of the handle 42 so that the lower portion 46 can be rotated relative thereto. This action removes the head member 32 from its aperture 16. since the main body portion 30 of the fastener 18 is not simultaneously rotated, the head portion 32 is simultaneously unthreaded therefrom. In a similar manner, the head portion 32 is returned to threaded engagement with both the aperture 16 of the plate 14 and the upper shaft portion 32 of the main body portion 30 after the desired surgical procedure is performed on the mandible 12.

When the locking plate 14 is operatively associated with the mandible 12 as shown in FIG. 1, the locking plate 14 is adjacent to but slightly displaced from the bone 12. In this regard, the flange 38 which is interdisposed between the upper and lower externally threaded portions 34 and 36 of the fasteners 18 limits downward translation of the removable head member 32. The thickness of the head member 32 is greater than the thickness of the locking plate 14. As a result, when a head members 32 is completely threaded on to the upper portion 34 of an associated fastener 18, the head member 32 extends rearward beyond the locking plate 14 and the locking plate 14 is displaced from the bone 12. Such spacing reduces absorption of the bone which would otherwise be present if the locking plate 14 were to directly contact the bone 12.

Figures 7, 8:
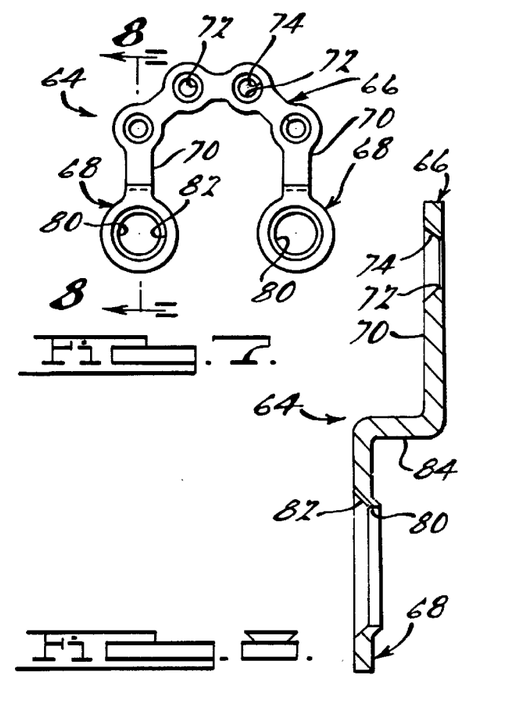
FIG. 7 is a view of the auxiliary reinforcement member of FIG. 1.
FIG. 8 is an enlarged cross-sectional view taken along the lines 8—8 of FIG. 7.

With continued reference to FIG. 1 and additional reference to FIGS. 7 and 8, an auxiliary reinforcement member 64 is illustrated. FIG. 1 shows the auxiliary reinforcement member 64 operatively interconnecting a portion of the mandible 12 and the locking plate 14. The auxiliary reinforcement member 64 is intended to reinforce fractured or otherwise weakened portions of the bone 12.

In the exemplary embodiment illustrated, the auxiliary reinforcement member 64 is shown to generally include a bone attachment portion 66 and a pair of plate attachment portions 68. The plate attachment portions 68 are each interconnected to the bone attachment portion 66 through a leg portion 70. In the embodiment illustrated, the bone attachment portion 66 is generally arcuate in shape and includes a plurality of apertures 72. Each of the apertures 72 includes a countersunk portion 74. The apertures 72 are each adapted to receive a threaded fastener 76. The threaded fastener 76 includes a head 78 adapted to seat in the countersunk portion 74 of the aperture 72 and a threaded shaft (not shown) for engaging a portion of the mandible 12. The head 78 of the threaded fastener 76 further includes a generally rectangular aperture substantially identical to the aperture 54 of the threaded fastener 18. As such, the threaded fastener 76 may be inserted and removed with the first drive portion 48 of the tool 40. Alternatively, a separate tool may be used to drive the fastener 76.

The plate engagement portions 68 of the auxiliary reinforcement member 64 are generally circular in shape and include an aperture 80 having a countersunk portion 82. As shown in FIG. 1, each of the plate engaging portions 68 may be interconnected to the plate 14 with a head portion 32 of the fastener 18. A tapered flange portion 84 (shown in FIG. 4) of the removable head 32 seats in the countersink 74 of the aperture 72 thereby securing the auxiliary reinforcement member 64 to the plate 14 when the external threads of the removable head 32 are engaged with the internal threads of one of the plate apertures 16.

As shown more specifically in FIG. 8, each of the legs 70 are connected to its associated plate engagement portion 68 through an intermediate portion 85. The intermediate portion 85 extends perpendicular to the plane of the bone engagement portion 66 and the plane of the plate engagement portion 68. As a result, the plate engagement portion 66 is stepped down from bone engagement portion 68.

Figure 9:
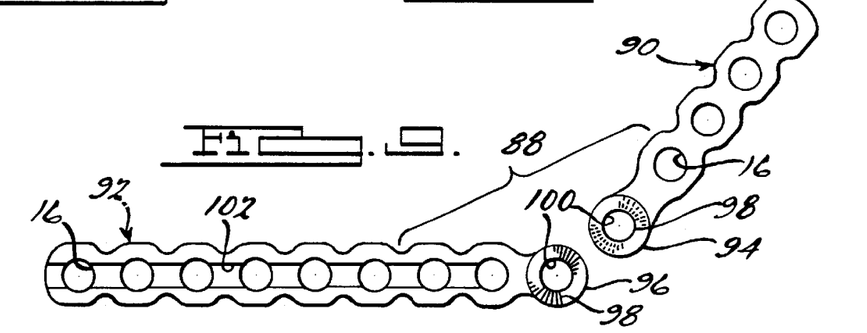
FIG. 9 is an illustration of a pair of links in accordance with the teachings of the present invention.
Figure 10:
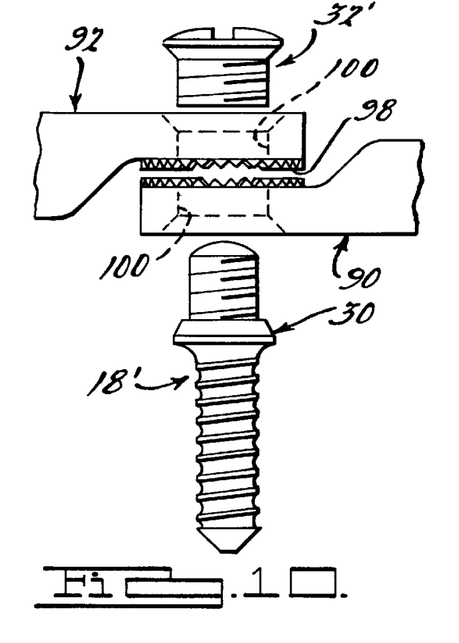
FIG. 10 is a fragmentary exploded view of the pair of links of FIG. 9 and a cooperating anchor member.

With reference to FIGS. 9 and 10, a link system 88 constructed in accordance with the teachings of the present invention is illustrated. The link system 88 is intended to function as an alternative structure for the locking plate 14 and generally includes first and second links 90 and 92 which are preferably shown to be substantially linear in shape. Each of the links 90 and 92 includes a plurality of apertures 16 substantially identical to the apertures 16 of the locking plate 14. The apertures 16 of the first and second links 90 and 92 are internally threaded and function with one or more fasteners 18 as discussed above. It will be understood by those skilled in the art that either of the first and second links 90 and 92 may have a non-linear shape.

The first and second links 90 and 92 are preferably shown to include cooperating ends 94 and 96, respectively. To provide means for positively locating the first and second links 90 and 92 angularly relative to one another, the cooperating ends 94 and 96 of the first and second links 90 and 92 are each provided with serrations 98 which circumferentially surround an aperture 100. In the embodiment illustrated, the apertures 100 surrounded by the serrations 98 are not internally threaded. The first and second links 90 and 92 are secured to one another and in turn to the bone 12 by a fastener 18'. The fastener 18' is largely identical to the fastener 18 described in connection with FIGS 4–6. As such, identical reference numerals will be used to identify equivalent elements. The fastener 18' differs from the fastener 18 in that the external diameter of the head 32 is smooth, thereby permitting the first and second link members 90 and 92 to rotate relative to the fastener 18', effectively defining a pivot.

In the embodiment illustrated, the second link 92 of the link system 88 is shown to include a longitudinally extending groove 102. The groove 102 intersects the apertures 16 of the link 92 and functions to increase bending strength of the link 92. It will be understood by those skilled in the art that a similar groove may be added to the first link 90 and also incorporated into the locking plate 14 of FIGS. 1 and 2.

In the preferred embodiment, the fasteners 18 and 18' are constructed from 6AL4V titanium (ti64). However, it will be appreciated by those skilled in the art that other materials of having suitable strength and biocompatable characteristics may be incorporated.

Turning to FIGS. 11 and 12, a link reinforcement member 104 of the system 10 of the present invention is illustrated. FIG. 11 illustrates the link reinforcement a member 104 operatively interconnected to a locking plate 14 to which is substantially identical to that described above with respect to FIGS. 1 and 2. The locking plate 14 is in turn secured to the mandible 12. FIG. 12 is a cross-sectional view illustrating the cooperating relationship between the locking plate reinforcement member 104 and the locking plate 14. The link reinforcement member 104 is intended to reinforce the locking plate 14 at areas where significant bone mass may be absence.

The reinforcement member 104 is illustrated to include a plurality of apertures 106 adapted to align with apertures 16 of the locking plate 14. As shown most clearly in FIG. 12, the locking plate reinforcement member 104 defines a groove 108 adapted to receive the locking plate 14. In use, the plate reinforcement member 104 is placed over the locking plate 14 such that the locking plate 14 is positioned within the groove 108 and the apertures 106 are aligned with the apertures 16. To secure the reinforcement member 104 to the plate 14, a head portion 32 of the fastener 18 is used in a manner substantially identical to the interconnection of the auxiliary reinforcement plate 64 and the locking plate 14. In this regard, the tapered portion 84 of the removal head 32 seats in a countersink portion 108 of the aperture 106 and the removable head 32 threadably engages an aligning aperture 16 of the locking plate 14. If desired, a main body portion 30 of the fastener 18 may also be employed for purposes of providing an additional point of attachment to the mandible 12.

Figure 16:
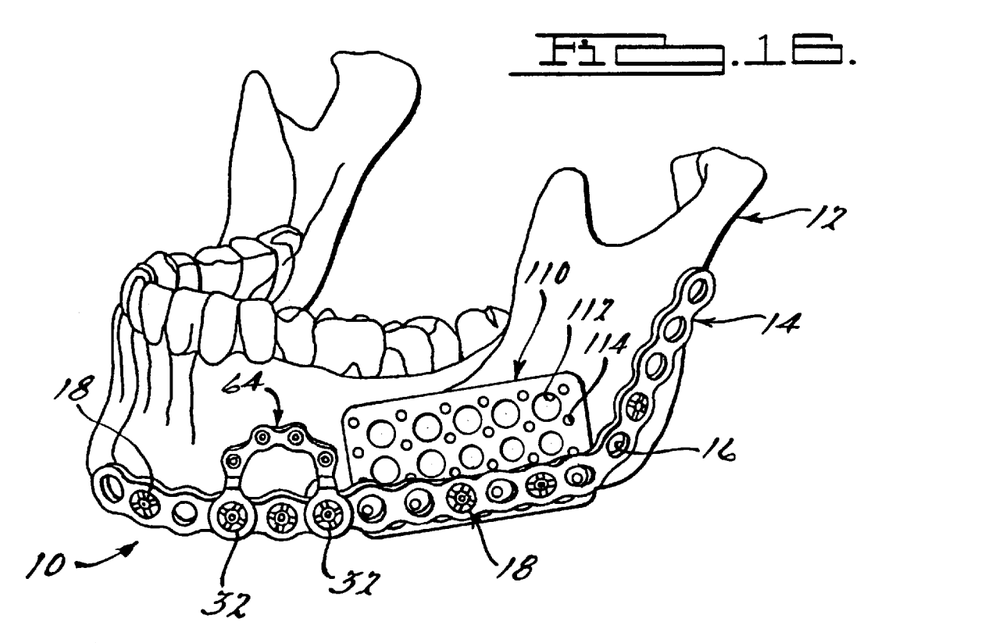
FIG. 16 is a perspective view similar to FIG. 1, shown incorporating a mesh reinforcing member of the mandibular osteosynthesis system of the present invention.
Figures 17, 18:
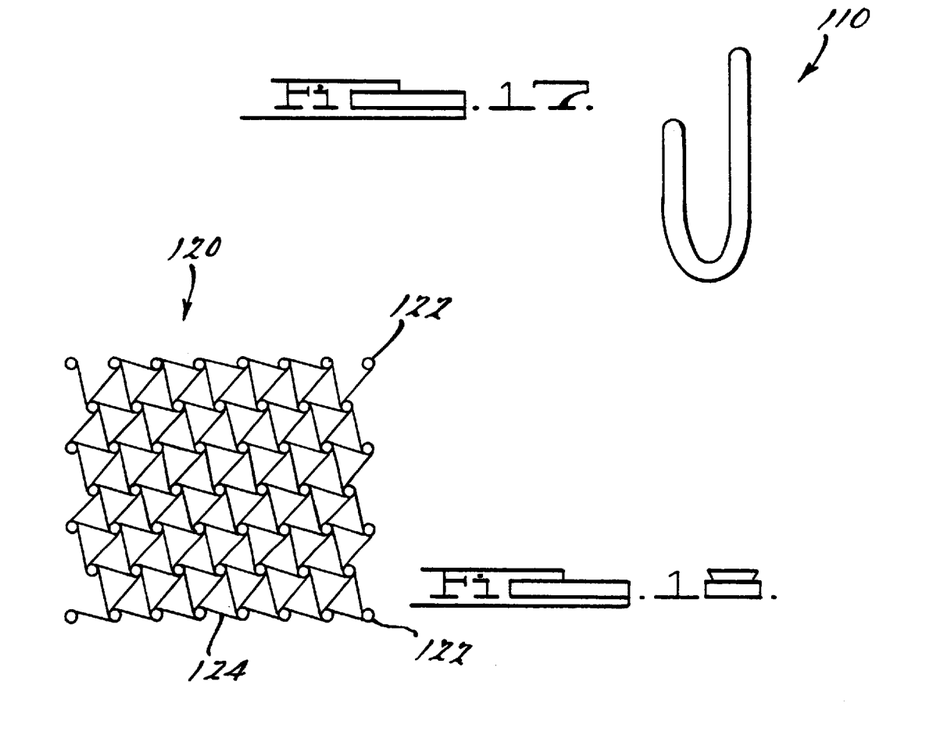
FIG. 17 is an enlarged side view of the mesh reinforcing member of FIG. 16.
FIG. 18 is a front view of an alternative mesh reinforcing member.

Turning to FIGS. 16 and 17, a mesh reinforcement member 110 of the system 10 of the present invention is illustrated. FIG. 16 illustrates the mesh reinforcement member llo operatively interconnected to a reconstruction plate 14 which is substantially identical to that described above with respect to FIGS. 1 and 2. The plate 14 is in turn secured to the mandible 12. FIG. 17 is an enlarged side view illustrating of the mesh reinforcement member 110. The mesh reinforcement member 110 provides another manner for reinforcement at areas of the mandible 12 where a resection has been made or significant bone mass is otherwise absent. In the embodiment illustrated, the reconstruction plate is a locking plate 14. However, it will become apparent that the mesh reinforcement member 110 may alternatively be used with a non-locking plate (not specifically shown).

In one application, the mesh reinforcement member 110 is constructed from a flexible, memory-retaining material such as titanium. In other applications, it may be desirable to construct the mesh reinforcement member 110 from a reoorbdble material. One such material includes LactoSorb®, which is commercially available from W. Lorenz Surgical, Inc. of Jacksonville, Fla. LactoSorb® is a registered trademark of Biomet, Inc. of Warsaw, In. It will be readily appreciated that still other biocompatable materials may be used within the scope of the present invention.

The mesh reinforcement member 110 of the present invention is illustrated to include a repeating pattern having arger holes 112 aligned in rows and columns. The repeating pattern additionally includes smaller holes 114 similarly aligned in rows and columns. The smaller holes 114 are arranged such that each smaller hole 114 is positioned equally between four larger holes 112 for the repeating pattern. In other applications, the holes 112 and 114 may be of smaller or larger size. Also, it may be desired to configure the holes 112 or 114 in a shape other than a circle, including but not limited to an oval or hexagonal shape. In the embodiment illustrated, the smaller holes 114 are spaced so as to align with apertures 16 of the plate 14.

In use, the mesh reinforcing member 110 is provided in a generally U-shaped curved configuration. The mesh reinforcing member 110 is adjusted to the general shape of the cooperating bone surface. In the exemplary use shown in FIG. 16, a lower portion of the mesh reinforcing member 110 wraps around a lower edge of the mandible 12. The adjusted configuration of the mesh reinforcement member 110 is shown in side view in FIG. 17. Typically, desired surgical procedures are made to the bone 12 and the mesh reinforcement member 110 is subsequently adjusted to the particular desired configuration.

In one application, the mesh reinforcement member 110 may be secured to the plate 14 and in turn secured to the mandible 12 by the fasteners 18 which otherwise secure the plate 14 to the mandible 12. Alternatively, the mesh reinforcement member 110 can be secured to the plate 14 and the plate 14 can be independently secured to the bone 12, or the mesh reinforcement member can be independently secured to the bone 12 and subsequently secured to the plate 14.

FIG. 16 illustrates a pair of fasteners 18 securing the mesh reinforcing member 110 to the plate 14. The fasteners 18 are shown to extend through one of the smaller holes 114 in the mesh reinforcing member 110. It will be understood that additional fasteners (not specifically shown) may be used to further secure the mesh reinforcing member 110 to the mandible. Such additional fasteners may pass through other of the apertures 16 in the plate 14, or directly through one of the smaller holes 114 or larger holes 112 of the mesh reinforcing member 110. It will be further understood that a variety of screws can be used to secure the plate 14, including but not limited to reconstruction screws, standard fracture screws, or dedicated screws.

With final reference to FIG. 18 of the drawings, an alternative mesh reinforcing member 120 is illustrated. The mesh reinforcement member 120 is milled from titanium or other suitable material. A substantially identical mesh material is commercially available from W. Lorenz Surgical, Inc. of Jacksonville, Fla. for cranial mesh applications. The alternative mesh reinforcement member 120 has a repeating pattern including a plurality of smaller holes 122 joined by a webbing 124. The alternative mesh reinforcement member 120 may be more easily bent and configured to a desired contour. In certain applications, it may be desirable to incorporate larger holes into the alternative mesh reinforcement member 120 to a accommodate standard screws for attachment to the bone.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention. For example, the configuration of the plate 14 shown in the drawings is one example of a plate suitable for use with the teachings of the present invention. It will be understood by those skilled in the art that various other shapes may be employed. For example, the plate 14 may be straight, angled, curved or any combination thereof. In certain applications, the plate 14 may extend about the entire mandible 12.

What is claimed is:

1. A system for osteosynthesis of a mandible, the system comprising:
    an elongated locking plate having a plurality of internally threaded apertures;
    an auxiliary reinforcement member extending from the elongated locking plate;
    a first fastener securing a first end of the auxiliary reinforcement member to the elongated locking plate; and
    a second fastener securing a second end of the auxiliary reinforcement member to the elongated locking plate;
    wherein the auxiliary reinforcement member includes an arcuate portion interconnecting the first and second ends.

2. The system for osteosynthesis of a mandible of claim 1, wherein the first fastener threadably engages a first one of the plurality of internally threaded apertures.

3. The system for osteosynthesis of a mandible of claim 1, wherein the second fastener has a main body portion and a removable head member, the main body portion having an externally threaded lower shaft portion and an upper shaft portion, the removable head member being externally threaded for engaging a second one of the plurality of internally threaded apertures, the head member and the first fastener being interchangeable.

4. The system for osteosynthesis of a mandible of claim 1, wherein the auxiliary reinforcement member includes a plate attachment portion and a bone attachment portion, the bone attachment portion oriented parallel to and stepped from the plate attachment portion.

5. The system for osteosynthesis of a mandible of claim 4, wherein the plate attachment portion and the bone attachment portion are interconnected by an intermediate portion oriented perpendicular to the bone attachment portion and the plate attachment portion.

6. A system for osteosynthesis of a mandible, the system comprising:
    an elongated locking plate having a plurality of internally threaded apertures;
    an auxiliary reinforcement member extending from the elongated locking plate, the auxiliary reinforcement member including a plate attachment portion and a bone attachment portion, the bone attachment portion oriented parallel to and stepped from the plate attachment portion; and
    a first fastener securing the auxiliary reinforcement member to the elongated locking plate;
    wherein the plate attachment portion and the bone attachment portion are interconnected by an intermediate portion oriented perpendicular to the bone attachment portion and the plate attachment portion.

7. The system for osteosynthesis of a mandible of claim 6, wherein the first fastener threadably engages a first one of the plurality of internally threaded apertures.

8. The system for osteosynthesis of a mandible of claim 6, wherein the auxiliary reinforcement member includes a first end attached to the elongated locking plate with the first fastener and a second end attached to the elongated locking plate with a second fastener.

9. The system for osteosynthesis of a mandible of claim 6, wherein the auxiliary reinforcement member includes first and second ends attached to the elongated locking plate and an arcuate portion interconnecting the first and second ends.

10. The system for osteosynthesis of a mandible of claim 6, further including a second fastener for attaching the elongated plate member to the bone, the second fastener having a main body portion and a removable head member, the main body portion having an externally threaded lower shaft portion and an upper shaft portion, the removable head member being externally threaded for engaging a second one of the plurality of internally threaded apertures, the head member and the first fastener being interchangeable.

11. A method of surgically repairing a bone, the method including the steps of:
    providing an elongated locking plate including a plurality of apertures;
    providing an auxiliary reinforcement member; and
    securing the auxiliary reinforcement member to the elongated locking plate with a first fastener and a second fastener such that the auxiliary reinforcement member extends from the elongated locking plate, the first fastener threadabiy engaging a first aperture of the elongated locking plate, the second fastener including a removable head and upper shaft portion, the removable head threadably engaging a second aperture of the elongated locking plate and threadably engaging the upper shaft portion.

12. The method of surgically repairing a bone of claim 11, further comprising the step of removing the removable head from the upper shaft.

13. A system for osteosynthesis of a mandible, the system comprising:
    an elongated locking plate having a plurality of internally threaded apertures;
    an auxiliary reinforcement member extending from the elongated locking plate;
    a first fastener securing the auxiliary reinforcement member to the elongated locking plate, the first fastener threadably engaging a first one of the plurality of internally threaded apertures;
    a second fastener for attaching the elongated plate member to the mandible, the second fastener having a main body portion and a removable head member, the main body portion having an externally threaded lower shaft portion and an upper shaft portion, the removable head member being externally threaded for engaging a second one of the plurality of internally threaded apertures, the head member and the first fastener being interchangeable.

\* \* \* \* \*

UNITED STATES PATENT AND TRADEMARK OFFICE
CERTIFICATE OF CORRECTION

PATENT NO. : 6,325,803 B1
DATED : December 4, 2001
INVENTOR(S) : Brian S. Schumacher, Kevin T. Stone and Jeffrey A. Duncan It is certified that error appears in the above-identified patent and that said Letters Patent is hereby corrected as shown below:

Column 1,
Line 14, before "apparatus" insert -- and --.
Line 41, "desire" should be -- desired --.

Column 2,
Line 58, after "illustration" insert -- of --.

Column 3,
Line 20, "andibular" should be -- mandibular --.
Line 44, "mandibular" should be -- mandible --.

Column 4,
Line 31, "position" should be -- positioned --.

Column 5,
Line 1, delete "go".
Line 20, "SO" should be -- 50 --.
Line 36, "49" should be -- 46 --.
Line 36, "t[]e" should be -- the --.
Line 45, delete "the" and substitute -- to -- therefor.
Line 51, "since" should be -- Since --.
Line 66, "members" should be -- member --.

Column 7,
Line 25, delete "of".
Line 31, delete "to".
Line 39, "absence" should be -- absent --.
Line 62, "11o" should be -- 110 --.
Line 66, delete "of".

UNITED STATES PATENT AND TRADEMARK OFFICE
CERTIFICATE OF CORRECTION

PATENT NO. : 6,325,803 B1
DATED : December 4, 2001
INVENTOR(S) : Brian S. Schumacher, Kevin T. Stone and Jeffrey A. Duncan It is certified that error appears in the above-identified patent and that said Letters Patent is hereby corrected as shown below:

Column 8,
Line 12, "reoorbdble" should be -- resorbable --.
Line 20, "arger" should be -- larger --.

Column 9,
Line 9, delete "a".

Column 10,
Line 38, "thredably" should be -- threadably --.

Signed and Sealed this

Fourteenth Day of January, 2003

JAMES E. ROGAN
*Director of the United States Patent and Trademark Office*